Figure 3:
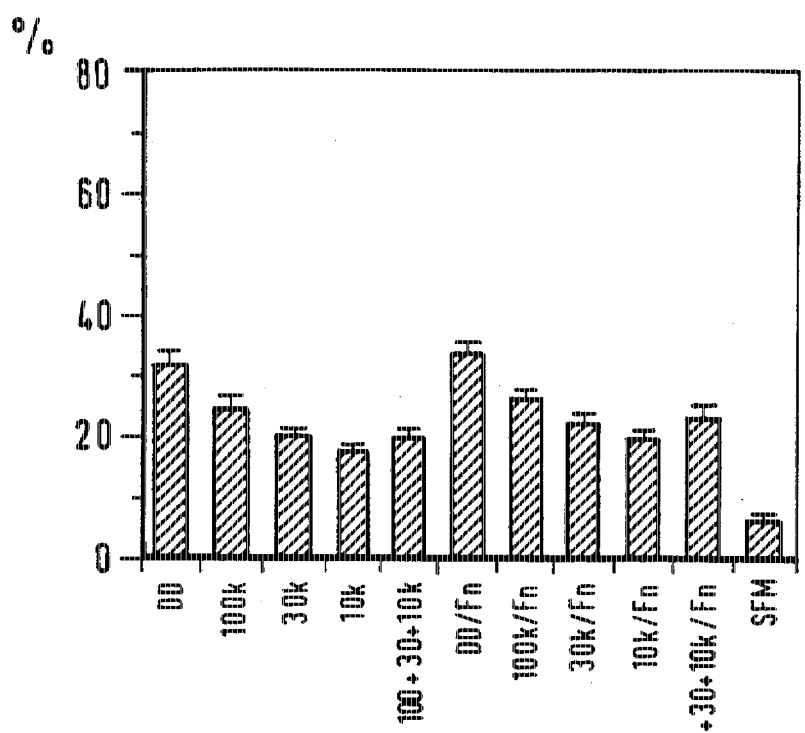

United States Patent [19]

Steele et al.

[11] Patent Number: 5,713,957
[45] Date of Patent: Feb. 3, 1998

[54] CORNEAL ONLAYS

[75] Inventors: John Gerard Steele, North Rocks; Brien A. Holden, Kingsford; Deborah Sweeney, Roseville; Dan O'Leary, Hurstville; Klaus Schindhelm, Cherrybrook, all of Australia; Antti Vannas, Helsinki, Finland; Graham Johnson, Peakhurst, Australia

[73] Assignees: CIBA Vision Corporation, Duluth, Ga.; The Commonwealth of Australia Commonwealth Scientific and Industrial Research Organization, Campbell, Australia

[21] Appl. No.: 646,287
[22] PCT Filed: Nov. 9, 1994
[86] PCT No.: PCT/EP94/03680
§ 371 Date: May 16, 1996
§ 102(e) Date: May 16, 1996
[87] PCT Pub. No.: WO95/13764
PCT Pub. Date: May 26, 1995

[30] Foreign Application Priority Data

Nov. 19, 1993 [AU] Australia ............................ PM2549

[51] Int. Cl.⁶ ............................................ A61F 2/14
[52] U.S. Cl. ................................................. 623/5
[58] Field of Search ........................... 623/5; 351/160 C

[56] References Cited

U.S. PATENT DOCUMENTS

| | | | |
|---|---|---|---|
| 4,621,912 | 11/1986 | Meyer | 351/160 |
| 4,624,669 | 11/1986 | Grendahl | 623/5 |
| 4,795,462 | 1/1989 | Grendahl | 623/5 X |
| 4,799,931 | 1/1989 | Lindstrom | 623/5 |
| 4,810,082 | 3/1989 | Abel, Jr. | 351/160 |
| 4,851,003 | 7/1989 | Lindstrom | 623/5 |
| 4,911,717 | 3/1990 | Gaskill, III | 623/11 |
| 4,994,080 | 2/1991 | Shepard | 623/5 |
| 5,171,318 | 12/1992 | Gibson et al. | 623/5 |
| 5,192,316 | 3/1993 | Ting | 623/5 |
| 5,244,799 | 9/1993 | Anderson | 435/240 |

FOREIGN PATENT DOCUMENTS

| | | |
|---|---|---|
| 3382089 | 4/1989 | Australia . |
| 0333344A2 | 3/1989 | European Pat. Off. . |
| 2218990 | 5/1989 | United Kingdom . |
| WO8900032 | 12/1989 | WIPO . |
| WO9103990 | 4/1991 | WIPO . |
| WO9107687 | 5/1991 | WIPO . |
| WO 9314133 | 7/1993 | WIPO . |

*Primary Examiner*—Mary Beth Jones
*Attorney, Agent, or Firm*—R. Scott Meece; Michael U. Lee

[57] ABSTRACT

Corneal onlays for use in surgical implantation into or onto the cornea of a mammal are described. The corneal onlays according to the invention have an optical axis region with optical characteristics which provide visual acuity therethrough and are comprised of a non-biodegradable non-hydrogel ocularly biocompatible material, characterized in that the onlay has a porosity sufficient to allow passage therethrough of tissue fluid components having a molecular fluid weight greater than 10,000 daltons so as to provide for a flux of tissue fluid between cells anterior of the implanted onlay and cells posterior thereof. The porosity of the optical axis region is such that it allows the flux of tissue fluid components whilst excluding ingrowth of ocular tissue. The onlay is further characterized by being adapted for epithelial recolonization. Also described are methods for correcting the optical property of an eye or altering the appearance thereof which comprises surgically implanting into or onto the cornea a corneal onlay as described above.

26 Claims, 2 Drawing Sheets

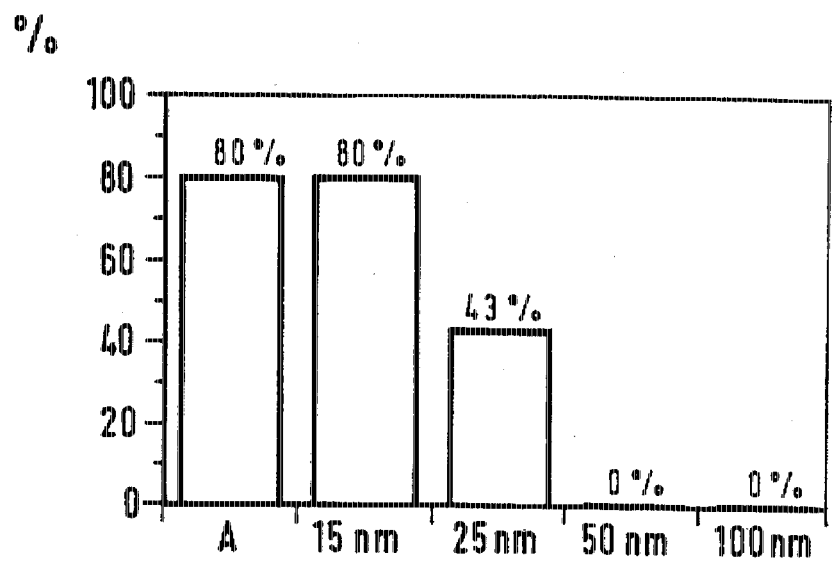
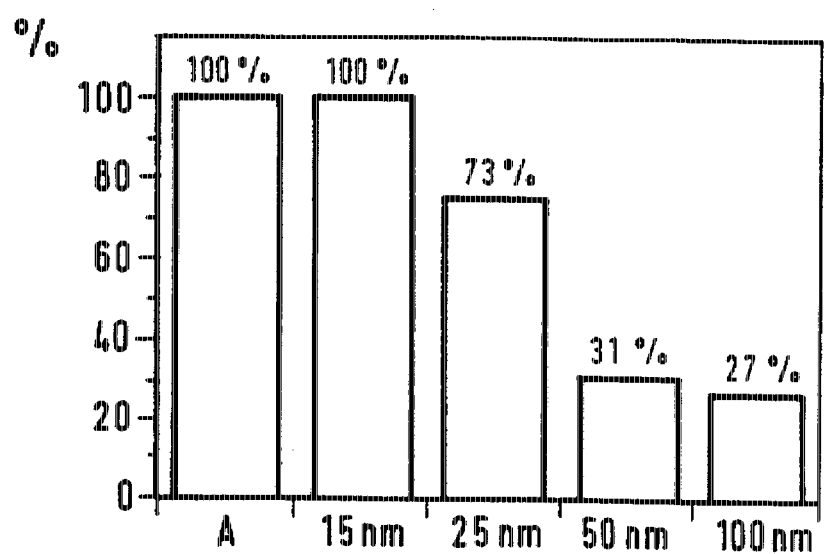

5,713,957

CORNEAL ONLAYS

This invention relates to the field of ophthalmology, and more particularly is directed to corneal implants.

The cornea is a complex layered structure comprising an outer layer of epithelial cells, Bowman's membrane posterior of the epithelial layer, the stroma posterior of the Bowman's membrane, Descemet's membrane posterior of the stroma, and the endothelium immediately posterior of Descemet's membrane. A number of surgical procedures involve implanting a lens structure into or onto one or more of these corneal components. In one form of eye surgery, the epithelial cell layer is removed and a corrective lens structure is placed and secured at the location where the cells are removed. In another form of eye surgery, a portion of the layer of epithelial cells is removed and a wedge-shaped annulus from Bowman's membrane and the underlying stroma is removed. An incision is then made from the posterior end of the resulting groove radiating outwardly in an annular zone to define a flap. A corrective lens structure is then attached by inserting the wing of the lens structure beneath the cornea/flap and sunning it in place. A corrective lens structure can also be placed entirely within the stroma. This surgical procedure involves making an incision in the cornea to gain access to the stroma and also involves disrupting the stroma by placing a lens structure therein.

The aforementioned corneal corrective surgeries are employed for the treatment of severe visual disturbances such as those associated with excessive or insufficient corneal curvature, traumatic injury to the cornea, for contact lens intolerant patients and the like. These procedures are generally known as keratoplasties.

It has previously been recognized that implanted corneal prostheses must be effectively anchored to cornea/tissue, and provide permeability to gas, metabolites and nutrients (particularly glucose). Apart from surgical techniques and mechanical fixation with sutures and the like to fix implants in place, previous proposals have employed attachment factors which coat the implant (see, for example, U.S. Pat. Nos. 4,715,858; 5,171,381; and 5,192,316). With regard to questions of permeability, prior proposals have included the use of hydrogel forming polymers of high-water content on the basis of their permeability to glucose and gas exchange characteristics. We have found that hydrogels, whilst porous to glucose, nutrients and metabolites, are not porous toward protein. Hydrogels and like "porous" polymers block the free movement of proteins and other high molecular weight tissue fluid components and so compartmentalize the tissue anterior to a corneal implant from that beneath the implant. This has significant deleterious effects as will be hereinafter described. Hydrogels also lack the requisite mechanical properties necessary for ocular implants. For example, hydrogel ocular implants described in Australian Patent No. 623137 shrink by about 22% (that is shrinkage from initial volume) when placed in physiological saline (see page 16, lines 19 to 24 of Australian Patent No. 623137). Clearly such materials would not be appropriate for implantation into the eye. Moreover, cells attach very poorly to hydrogel polymers with the result that epithelial recolonization of hydrogel implants would be impeded.

It has also previously been proposed to provide corneal implants with holes for the passage of nutrients and fluids from the lower layers of the cornea through the implant to the upper layer of the cornea. These proposals suffer the disadvantages that the holes provided are too small to allow passage of proteins, or alternatively, are of such a diameter that visual acuity is effected either by direct distortion of light passing through the implant or by tissue ingrowth into the implant obscuring vision.

We have now surprisingly found that the flow of high molecular weight tissue fluid components such as proteins and glycoproteins (for example, growth factors, peptide and protein hormones, and proteins associated with the transport of essential metals) and the like, across a corneal implant, that is, from epithelial cells to stromal cells and even to the endothelial layer and beyond, is essential for long term maintenance and viability of tissue anterior and posterior to a corneal implant. In the context of implants within the corneal epithelium, wherein an area of epithelial cells are debraded and an implant inserted either within the remaining epithelium or on the basement membrane, the flow of tissue fluid components necessary for the all important coverage of an implant with adhered epithelial cells is critical. This includes tissue fluid flowing from the stromal tissue beneath the implant towards the tissue on the anterior surface (and particularly the epithelial tissue) during the process of the initial coverage of the anterior surface with epithelial cells, and the flow of proteinaceous components from these epithelial cells to the stromal tissue and beyond.

We have surprisingly found that the corneal implants of the prior art prevent the passage of high molecular weight proteins and glycoproteins (such as those having a molecular weight up to or greater than 10,000 daltons and up to and in excess of 200,000 daltons or more), and adversely effect the formation of an epithelial layer over an anterior surface of a lens implant inserted within the epithelial layer of the cornea. Likewise, tissue posterior to corneal implants suffers from stromal degeneration which is believed to result from the inability of high molecular weight proteinaceous components to pass from epithelium tissue to stromal tissue.

This invention is particularly directed towards an implant to be placed beneath, within, or through corneal epithelial tissue, or within the corneal stroma or other tissue layers of the cornea. For convenience, all such implants will be referred to hereafter as corneal onlays.

In accordance with the first aspect of this invention there is provided a corneal onlay for use in surgical implantation into or onto the cornea of a mammal, said onlay having an optical axis region with optical characteristics which provide visual acuity therethrough, said onlay being comprised of a non-biodegradable non-hydrogel ocularly biocompatible material, and characterized in that said onlay has a porosity sufficient to allow passage therethrough of tissue fluid components having a molecular weight greater than 10,000 daltons, thereby providing for a flux of tissue fluid between cells an anterior of the implanted onlay and cells posterior thereof, wherein the porosity of the optical axis region is such that it allows the flux of tissue fluid components whilst excluding ingrowth of ocular tissue, and wherein said onlay is adapted for epithelial recolonization.

In another aspect of the invention there is provided a method for correcting the optical properties of an eye or altering the appearance thereof comprising, surgically implanting into or onto the cornea a corneal onlay for use in surgical implantation into or onto the cornea of a mammal, said onlay having an optical axis region with optical characteristics which provide visual acuity therethrough, said onlay being comprised of a non-biodegradable non-hydrogel ocularly biocompatible material, and characterized in that said onlay has a porosity sufficient to allow passage therethrough of tissue fluid components having a molecular weight greater than 10,000 daltons, thereby providing for a flux of tissue fluid between cells anterior of the implanted onlay and cells posterior thereof, wherein the porosity of the optical axis region is such that it allows the flux of tissue fluid components whilst excluding ingrowth of ocular tissue, and wherein said onlay is adapted for epithelial recolonization.

The corneal onlay may comprise the same visual acuity across its dimensions, as do conventional contact lenses. However, as visual acuity is only required for that portion of the onlay which covers the pupil, hereafter referred to as the optical axis region, it is preferred to provide a corneal onlay having an optical axis region having a porosity sufficient to allow passage therethrough of tissue fluid components having a molecular weight up to or greater than 10,000 daltons, but which excludes ingrowth of ocular tissue. In such a situation, the periphery of the onlay surrounding the optical axis region may define a skirt having a porosity sufficient to permit ingrowth of ocular tissue so as to facilitate anchorage of the onlay to the cornea.

The porosity of the corneal onlay over the optical axis region of the eye allows the flow or flux of tissue fluid components comprising high molecular weight protein, as well as small molecular weight nutrients such as glucose and respiratory gases through the onlay. The porosity of the onlay allows for protein species having a molecular weight of several thousand daltons up to several hundred thousand daltons or more to freely pass through the corneal layers as hereinbefore described. It is the passage of high molecular weight proteinaceous components, such as growth factors, hormones, signalling proteins, molecular transmitters, and transport proteins such as transferrin which transport essential metal ions, which provide for the maintenance, integrity and health of tissues posterior and anterior to an implanted corneal onlay. Our experiments have shown that the passage of proteins and other components having a molecular weight of at least 10,000 daltons is essential for tissue integrity and maintenance. Having said this, it is clear that the passage of proteinaceous and other components having a molecular weight less than 10,000 daltons is also important and this invention therefore embraces the passage through a corneal onlay of nutrients, metabolic gases, and particularly proteins, carbohydrates and lipids having a molecular weight up to 300,000 daltons or more, such as 500,000 daltons, or even up to 1,000,000 daltons.

The corneal onlay as herein described, is capable of being surgically associated with, and preferably attached to, a living cornea so as to change its optical properties (such as correct vision deficiencies of the eye) or to change the appearance of the eye, such as coloration of the pupil.

The porosity of the corneal onlay may be provided by virtue of the material from which the onlay is formed, that is, by the inherent porosity of the material. Alternatively, pores may be introduced into the material from which the onlay is formed by various procedures well known in the art such as those described in WO 90/07575, WO 91/07687, U.S. Pat. No. 5,244,799, U.S. Pat. No. 5,238,613, U.S. Pat. No. 4,799,931 and U.S. Pat. No. 5,213,721.

Pores may be formed after production of the onlay shape (such as by polymer casting), or in bulk material prior to onlay shape formation. Such procedures may involve:

i) Usage of sparks, or lasers to burn holes through the onlay or onlay material Pores may be conveniently produced by using excimer lasers, such as a pulse type laser under microprocessor control as described, for example, in WO 91/07687;

ii) Repetitive drawing of polymeric material as described in U.S. Pat. No. 5,213,721;

iii) Multiphase formation processes followed by chain polymerization such as described in U.S. Pat. No. 5,238,613.

Alternatively, porosity may be provided by an interpenetrating network of holes throughout the onlay material prepared such as by polymerization in the presence of an insoluble material. Subsequent removal of the insoluble material gives rise to interstices throughout the formed polymer material.

Regardless of the methods of formation of the requisite porosity of the onlay of the invention, the onlay must have a porosity sufficient to admit proteins of a molecular weight up to and greater than 10,000 daltons, such as from 10,000 to 1,000,000 daltons, but not sufficient to admit cells and thus tissue invasion into the optical axis region of the corneal onlay. Where porosity of the onlay is provided by pores, the optical axis region comprises a plurality of pores, the number of which is not in any way limiting on the invention, but which is sufficient to provide flow of tissue components from the anterior to posterior regions of an implanted onlay. By way of example only, the number of pores provided in the onlay may range from 200 pores per square millimeter to 300,000 pores per square millimeter or more. Preferably, the pores formed within the optical axis region are in the range of 5 nanometers to $15 \times 10^3$ nanometers in diameter. Pores of this size within the optical axis region would not cause refraction of visible light to an extent that would cause any problem with regard to vision correction. More preferably, the pores in the optical axis region have a diameter of from 15 to 300 nanometers, and even more preferably from 20 to 150 nanometers in diameter. It is to be understood that the term pore does not put any geometric limitation on the nature of the pores which may be of regular or irregular morphology. In this context the term "average width" may be preferable to the term "diameter". Within the above mentioned preferred diameters, it should be recognized that not all pores may be of the same diameter, but may vary within the range given.

Outside of the optical axis region, the onlay may have the same porosity as the optical axis region, that is, allowing passage through the onlay of small molecular weight nutrients, respiratory gases, and proteinaceous and other components of tissue fluid having a molecular weight up to and greater than 10,000 daltons (for example, up to 1,000,000 daltons or more) whilst being of a porosity which specifically excludes tissue ingrowth. Alternatively, this region of the onlay surrounding the periphery of the optical axis region, which may be referred to as the skirt, may allow the ingrowth of cells of the cornea thereby assisting in anchorage of the onlay to the eye. In this embodiment, the skirt may contain a plurality of pores of diameter of 20 microns or more, preferably 50 microns to 1,000 microns, more preferably 50 to 500 microns, and even more preferably 50 to 300 microns. Pores may be formed in the skirt in the same manner as that described above for the production of pores in the optical axis region of the onlay.

Porosity in the skirt may be an inherent feature of the material from which the skirt is formed. In this regard it is to be appreciated that the skirt may be formed of the same material as the optical axis region and may be integral therewith. In this situation, pores of differing diameter may be formed in the optical axis region and the skirt. Alternatively, the skirt may be formed in a distinct and separate manner to that of the optical axis region (for example, by polymerization in the presence of an insoluble agent such as glucose which is subsequently dissolved from a polymerized matrix to give a highly porous interpenetrating network), such that whilst formed of the same material as the optical axis region, the skirt has a much greater porosity thereby allowing tissue ingrowth. Alternatively, the skirt may be formed of a different material from the optical axis region, which material is of a higher porosity than the optical axis region so as to allow tissue ingrowth. The skirt may be processed in a manner to produce high porosity such as by preparing a coherent mass of melt drawn fibres having an interconnecting network of pores, such as fibres made of a polyolefin material, which is applied to the optical axis region. The skirt may, for example, be formed from a highly porous ceramic material which is fused to the optical axis region such as by solvent welding, heat fusion or use of adhesives. Highly porous ceramics which facilitate tissue ingrowth are well known (see, for example, J. Biomed. Mater. Res. Symp, No 4, pp 1–23, 1973).

The corneal onlay may be prepared from any one of the known natural or synthetic polymeric materials with the requisite mechanical properties such as polymers and copolymers of the classes commonly known as acrylics, polyolefins, fluoropolymers, silicones, styrenics, vinyls, polyesters, polyurethanes, polycarbonates, cellulosics or proteins such as collagen based materials. Hydrogel polymeric compositions are specifically excluded due to their propensity of shrinkage, lack of porosity to high molecular weight species, and poor cellular attachment properties.

Where a mixture of polymeric materials is used in the production of the corneal onlay, these materials may be copolymerized according to techniques well known in the art to give a resultant polymeric network. As mentioned above, the skirt may be formed of different polymeric or other materials than the optical axis region so as to allow tissue ingrowth, this being a function of greater porosity. The skirt region may be formed from one or more of the aforementioned polymers, ceramics or any other biocompatible non-biodegradable material having pores with a diameter greater than about 20 microns so as to allow tissue ingrowth.

The corneal onlay of this invention may be produced according to standard techniques for the production of corneal onlays as are well known in the art. Clearly the precise techniques used for the polymerization of polymers, copolymers, mixtures thereof, production of ceramics, and the joining of optical axis region to skirt where necessary, will depend upon the nature of the materials employed, with appropriate methodologies being adopted for respective materials according to conventional procedures.

The corneal onlay may be shaped during or at the conclusion of its production process according to standard milling, polishing, and/or shaping procedures as are well known in the field for the production of corneal prostheses. By way of example, the corneal onlay produced by polymerization is formed to shape either by moulding during polymerization, or by lathing of a preformed button. Alternatively, the optical axis region may be first formed to shape, for example, by either moulding or lathing of a preformed button, whereafter a skirt is attached to the periphery of the optical axis region by polymerization thereabouts. Alternatively, the optical axis region may be attached to a porous outer skirt, for example, by dipping the skirt in acetone and pressing the two together. Alternatively, an optically acceptable adhesive may be used of materials fused together by the application of heat such as generated by a pulse laser. A skirt may first be formed having an annular orifice, within which the optical axis is formed either by polymerization of fixation of a pre-formed button.

The onlay or a portion thereof may be coloured with one or more pigments or dyes as are well known in the field. Coloured onlays, and particularly colouration around the pupil area, will result in change of eye coloration on implantation.

The corneal onlay according to this invention is adapted for epithelial recolonization. By this is meant that the polymeric substance from which the onlay is formed does not inhibit cellular attachment or motility. Additionally, the respective surfaces of the onlay may be modified as is hereinafter described to facilitate cellular attachment.

The outer posterior and anterior surface of the corneal onlay may be modified by the application of a polymer having pendant groups capable of being converted to reactive functional groups which are thereafter capable of covalently coupling to the onlay surface. For example, a surface modifying composition may comprise a poly amino acid, such as polylysine, where, for example, about 10 mol percent of pendant groups are capable of being convened to nitrene functional groups. The modified surface may of itself, stimulate the adhesion of cells adjacent to the implanted onlay, such as epithelial cells, or cells of the stroma. Alternatively, the modified surface may be coated with one or more components which promote the growth of tissue adjacent to the implanted onlay. For example, such materials include fibronectin, laminin, chondroitan sulphate, collagen, cell attachment proteins, anti-gelatine factor, cold-insoluble globulin, chondronectin, epidermal growth factor, mussel adhesive protein, thrombospondin, vitronectin, and various proteoglycans, and/or derivatives of the above and mixtures thereof. Fibronectin, derivatives of fibronectin, epidermal growth factor, derivatives of epidermal growth factor and mixtures thereof are particularly useful. Alternatively, the corneal onlay itself without surface modification may be directly coated with one or more components which promote the growth of tissue adjacent to the implanted onlay and/or cell adhesion to the onlay. These components may be any component or components which provide cell adhesion and/or promote cell growth such as growth factors and adhesion factors. Preferred materials are those detailed in connection with the application to a surface modified corneal onlay. Preferably, the coating of components which promote the growth of tissue adjacent to the implanted onlay are covalently bonded to the onlay, without effecting the optical properties thereof. As a result of surface modifications, or by virtue of inherent properties of the onlay, the onlay of this invention is adopted for epithelial recolonization.

The corneal onlay according to the invention described herein is distinct and superior to prior art proposals in that it provides an effective flow of high molecular weight tissue fluid components to the anterior surface from the tissue beneath the implant which serves to support and to stimulate the coverage of the anterior surface of the implant with corneal epithelial cells through the processes of migration from the adjacent tissue and stratification, and to support the maintenance of the epithelial tissue that covers the implant, or indeed any other tissue which covers the implant. Transcorneal signalling is provided, for example, during the initial period after implantation, such as during coverage of the implant with epithelium, and furthermore provides for the porosity of the implant towards therapeutic compounds applied to the anterior surface of the implant.

The corneal implant according to this invention may be inserted into the eye according to established keratectomy procedures as are well known in the field.

This invention will now be described with reference to the following non-limiting Figures and Examples.

FIGURES

FIG. 1: is a histogram which depicts the percentage (%) of animals with corneal ulcers for specific membrane pore sizes. Column A represents the membrane materials Cuprophan/Gambrane.

FIG. 2: is a histogram which depicts the percentage (%) of animals with epithelial and anterior stromal thinning for specific membrane pore sizes. Column A represents the membrane materials Cuprophan/Gambrane.

FIG. 3: is a histogram which shows bovine corneal epithelial cell attachment to tissue culture polystyrene (TCPS) in fractionated serum after twenty four hours. The X-axis represents the medium. The Y-axis represents the percentage cell number of control, wherein the control=DD/Fn at day 6, set at 100%. DD represents serum free culture medium and 20% (v/v) fibronectin and vitronectin-depleted serum; "100k" represents serum-free culture medium, to which was added 20% (v/v) of Fraction 1, having serum factors of 1000 to 100,000 daltons in size; "30k" represents serum-free culture medium, to which was added 20% (v/v) of serum factors of 1000 to 30,000 daltons in size; "10k" represents serum-free culture medium, to which was added 20% (v/v) of serum factors of 1000 to 10,000 daltons in size; "100+30+10k" represents serum-free culture medium, to which was added 20% (v/v) of serum factors of 1000 to 100,000 daltons in size; "DD" is serum-free culture medium+20% (v/v) Fibronectin- and Vitronectin-depleted serum (not fractionated as to size); SFM is serum free culture medium; and Fn denotes that the tissue culture polystyrene surface was precoated with fibronectin.

Figure 4:
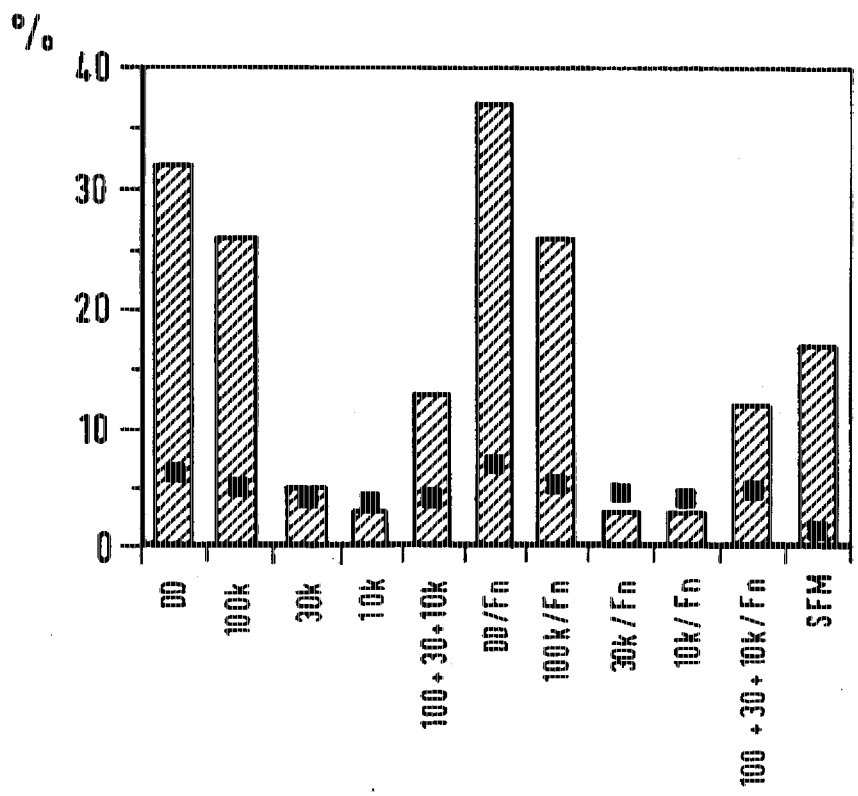

FIG. 4: is a histogram which shows corneal epithelial cell outgrowth on tissue culture polystyrene (TCPS) in fractionated serum after six days culture. The X-axis represents the medium. The Y-axis represents the percentage cell number 24 hr/5 (control at day 6); cell outgrowth 6 days/24 hr (wherein the hatched portion of the column represents the outgrowth, and the black squares represent the cell number). "DD" is serum-free culture medium+20% (v/v) Fibronectin- and Vitronectin-depleted serum (not fractionated as to size); "100k" represents serum-free culture medium, to which was added 20% (v/v) of Fraction 1, having serum factors of 1000 to 100,000 daltons in size; "3.0k" represents serum-free culture medium, to which was added 20% (v/v) of serum factors of 1000 to 30,000 daltons in size; "10k" represents serum-free culture medium, to which was added 20% (v/v) of serum factors of 1000 to 10,000 daltons in size; "100+30+10k" represents serum-free culture medium, to which was added 20% (v/v) of serum factors of 1000 to 100,000 daltons in size; SFM is serum free culture medium; and Fn denotes that the tissue culture polystyrene surface was precoated with fibronectin.

EXAMPLE 1

Passage of Macromolecules Across the Cornea is Essential for Maintenance of Normal Corneal Structure/Integrity Membranes of differing pore size were implanted into the eyes of cats to determine the effects of facilitating or blocking the flux of high molecular weight tissue fluid components across the cornea, both posterior and interior of a corneal implant.

In a first experiment, dialysis membranes with a 1.4 nanometer pore size were implanted into the cornea of cats. These membranes, whilst allowing the passage of glucose, amino acids, water and respiratory gases, block the passage of components having a molecular weight greater than 10,000 daltons. Both the corneal epithelium and stroma Of test animals lost integrity over the test period of four weeks. This experiment shows that tissue components having a molecular weight greater than 10,000 daltons, namely proteins and glycoproteins, are essential for corneal integrity.

Four adult cats were then used in a more detailed study.

A. Baseline Measurements

Baseline measurements of corneal integrity including slit lamp evaluation were conducted. Details of corneal transparency, vessel hyperaemia and penetration, surface characteristics, opacities, etc, were assessed.

B. Experimental Design

Two types of membrane, Nuclepore Filter (polycarbonate) and dialysis membrane (polycarbonate/PEG), were used in this study (Table 1). Prior to implantation, the membranes were trephined to diameter of 12 mm. The membrane used for Cat 2 had holes formed at the periphery thereof of 20 to 30 micrometers formed using a laser. The Nuclepore Filters were rubbed with Miraflow contact lens cleaner, then rinsed and autoclaved in sterile isotonic saline.

The dialysis membrane was rinsed and autoclaved in sterile isotonic saline after laser perforation.

TABLE 1

Membrane and Surgical Details

| Cat No | Implanted Eye | Membrane Type | Membrane Pore Size (μm) | Contralateral Sham Eye (Y/N?) |
|---|---|---|---|---|
| 1 | Left eye | Polycarbonate | 0.05 | No |
| 2 | Left eye | Polycarbonate/PEG | •Non-perforated: <0.0014; •Perforations: 20–30 | No |
| 3 | Right eye | Polycarbonate | 0.05 | Yes |
| 4 | Left eye | Polycarbonate | 0.1 | Yes |

C. Surgical Procedure

1. The cats were anaesthetised to a depth of stage 3—plane 2.
2. A diamond knife was used to make a 6 mm incision just inside the superior limbus.
3. A corneal dissector with a shape edge was used to form a lamellar pocket of 14 mm to 15 mm diameter.
4. Using plastic-tipped forceps, a membrane of 12 mm in diameter was inserted into the pocket.
5. In Cat 1 and Cat 2, the incision was closed with 9 to 0 mononylon. In Cat 3 and Cat 4, the incision was closed with 8 to 0 silk.

D. Follow up Evaluation

The eyes were assessed daily until clinical signs warranted termination (Table 2).

TABLE 2

Follow up Period

| Cat No | Number of Days Prior to Termination |
|---|---|
| 1 | 23 |
| 2 | 28 |
| 3 | 16 |
| 4 | Ongoing |

Euthanasia of cats was performed with an intravenous overdose of sodium pentobarbitone at 140 mg/kg of body weight.

E. Histology

Animal's eyes were removed rapidly after euthanasia. During the enucleation, fixative was dropped on to both eyes (2.5% glutaradehyde in 0.1M sodium cacodylate trihydrate, 2 mM calcium chloride, pH adjusted to 7.2 with 1M HCl, at 25° C.) at a sufficient ram to ensure that the anterior corneal surface remained moist. Immediately after death 0.3 ml of fixative was injected into the anterior chamber of each eye to aid the fixation of the posterior corneal surface.

Corneas were separated from the remainder of the eye and immersed in fixative for sixty hours at 4° C. Two 1 mm wide strips were cut from each cornea; one from periphery to centre along the superior-inferior axis; one from periphery to centre along the nasal-temporal axis.

RESULTS

Tables 3 and 4 provide a summary of the study design and findings.

I. Clinical Observations

The clinical appearance of the membranes, that is, the position and the size of the membranes, did not change throughout the observation period.

Deposition, oedema and neovascularization were more severe in implanted test eyes compared to the "sham" control eyes, which were not membrane implanted. These reactions appeared to be localized anterior to the membrane/pocket.

In the implanted eyes, 'deposits' were observed anterior to the membrane, particularly in the inferior region of the pocket two to three days after surgery.

For the "sham" eyes, the 'deposits' were mainly located in the central region of the pocket and appeared less dense than those observed in implanted eyes. The 'deposits' were of similar appearance to those for the implanted eyes, however, they did not progress to the same extent.

Corneal neovascularization started at the site of incision and continued to penetrate into the stroma overlying the membrane in all cats. However, corneal neovascularization regressed in one eye (Cat 4) during the study. The neovascularization observed was a complication of the surgical procedure rather than vessel growth due to lack of nutrients.

Anterior stromal 'deposits' and oedema were observed for Cat 1 Cat 3 and Cat 4 throughout the observation period.

Anterior stromal deposits, oedema and neovascularization were observed in the implanted area overlying the non-perforated region of the polycarbonate/PEG membrane. However, oedema and neovascularization were not observed in the area overlying the perforated region.

No clinically detectable changes to the stroma posterior to the membrane or to the endothelium were observed for any of the implanted eyes.

II. Histological Observations

The epithelium over the implanted membrane was reduced both in thickness and in the number of cell layers, compared to that found in the control cornea (unoperated and operated), in Cat 1 and Cat 3 respectively.

The epithelial cells of all the implanted eyes were changed, to some extent, in morphology as evidenced by an increase in the amount of extracellular staining, more granular nuclei and less well defined cytoplasm.

There was evidence of an inflammatory reaction in the corneal anterior and posterior to the membrane in Cat 2 and Cat 3. It manifested as swollen keratocytes, round and darkly staining cells, presumably neutrophils, and neovascularization in the posterior stroma.

There was a close association of the cellular changes with the implanted membrane in Cat 2. This is evidenced by:

the density of keratocytes increased dramatically approaching the membrane;

there was an increased number of small, round, darkly stained cells (possibly neutrophils) within the epithelium overlying the membrane and in the stroma anterior and posterior to the membrane;

in areas over the non-perforated region of the membrane, Bowman's layer appeared to have broken down;

granular material was observed adjacent to the stroma/membrane interface; the anterior stroma/membrane interface accumulated a thicker layer of granular material than that seen posteriorly in Cat 2;

morphological changes in cellular components of the epithelium appeared more obvious in areas overlying the non-perforated region of the membrane than over the perforated region;

The endothelium appeared intact and continuous in all the implanted eyes.

In Cat 3, a mass of keratocyte-like cells penetrated between Descemet's membrane and the anterior surface of the endothelial cells in the implanted eye. Several red blood cells were also observed adhering to the posterior face of the endothelium. These features were not observed in the "sham" eye.

As shown above implants which prevent the flux of high molecular weight proteinaceous tissue components across the cornea results in degeneration of the stroma and breakdown of the Bowman's layer as well as a loss of integrity of the corneal epithelium.

TABLE 3

Summary of Study Design and Findings

| Cat No | Eye (R/L) | Pocket (Y/N) | Pocket Depth | Membrane (Y/N) | Membrane Type | Membrane Pore Size ($\mu m$) | Days prior to Termination | Reason for Termination |
|---|---|---|---|---|---|---|---|---|
| 1 | R | N | — | N | — | — | 23 | |
| | L | Y | ½ stroma | Y | Polycarbonate | 0.05 | 23 | Tissue necrosis, oedema, neovascularization |
| 3 | R | Y | ⅔ stroma | Y | Polycarbonate | 0.05 | 16 | Neovascularization oedema |
| | L | Y | ⅔ stroma | N | — | — | 16 | |
| 4 | R | Y | ½ stroma | N | — | — | Ongoing | |
| | L | Y | ½ stroma | Y | Polycarbonate | 0.1 | Ongoing | |
| 2 | R | N | — | N | — | — | 28 | |
| | L | Y | ⅓ stroma | Y | Polycarbonate/PEG | •<1.4 $\mu m$ in non perforated region •variable: 20–30 in perforated region | 28 | Intrastromal necrosis |

TABLE 4

Summary of Findings Continued

| Cat No | Eye (R/L) | Other Clinical Observations | HISTOLOGICAL OBSERVATIONS | | | |
|---|---|---|---|---|---|---|
| | | | Epithelium | Stroma | Membrane Interface | Endothelium |
| 1 | R | Anterior stromal scar | Normal | Normal | Normal | Normal |
| | L | Streaks in stroma "Deposits" anterior to membrane | Thinned: cellular changes | Anterior: normal; Posterior: normal | Anterior: lined with granular material; Posterior: RBCs, debris lined with epi cells | Normal |
| 3 | R | Neovascularization; Oedema and haze "Deposits" anterior to membrane | Thinned: cellular changes | Anterior: "scar" tissue RBCs and inflammatory cells in superior quadrant; Posterior: activated keratocytes | Anterior: lined with granular material; Posterior: lined with epi cells and granular material | Keratocyte-like cells between Descemet's membrane and endothelium |
| | L | Inflammation: "Deposits" at level of pocket neo-vascularization | Normal | Normal | Normal | Normal |
| 4 | R | Oedema; Flare; Neovascularization; FB at level of endothelium; Bright endothelium | * | * | * | * |
| | L | Membrane decreasing in translucency | * | * | * | * |
| 2 | R | ---- | Normal | Normal | Normal | Normal |
| | L | Neovascularization; Oedema and haze anterior to membrane; Deposits posterior to central membrane | Normal thickness; Cellular changes and breakdown of Bowman's layer overlying intact membrane | Normal, except for region of neovascularization | Activated keratocytes lined anterior and posterior surfaces and filled perforations | Normal |

EXAMPLE 2

Onlay Porosity Required for Maintenance of Epithelial and Stromal Health

In this example onlays of varying porosity were surgically inserted into the eyes of adult cats (n=50). All cats were free of ocular or systemic disease. The details and characteristics of the membranes used in this study are set forth in Table 5.

TABLE 5

Membrane Materials and Specifications

| Names | Materials | Pore size (nm) | Porosity (ca %) | Diameter (mm) |
|---|---|---|---|---|
| Cuprophan | Regenerated cellulose | <15 | | 10 |
| Gambrane | Polycarbonate/P | 1.4 | | 12 and 8 |
| Poretics | Polycarbonate | 25 | 1.50 | 8 |
| Nucleopore | Polycarbonate | 100 | 2.36 | 12 and 8 |
| | | 50 | 1.20 | 12 and 8 |
| | | 15 | 0.10 | 8 |

Prior to implantation, the membranes were trephined to a diameter of 12 mm, 10 mm or 8 mm.

Surgical procedure and follow up evaluation was carried out according to Example 1. The number of animals which were implanted with specific membranes are set forth in Table 6.

TABLE 6

Summary of Animal Status for Each Membrane Type

| Number | Cuprophan | Gambrane | Poretics 25 nm | Nucleopore 100 nm | Nucleopore 50 nm | Nucleopore 50 nm |
|---|---|---|---|---|---|---|
| Total implanted | 2 | 3 | 8 | 15 | 16 | 6 |

Of the large amount of clinical observations and histological data assembled, the most pertinent data for an assessment of epithelial and stromal health following onlay membrane insertion is corneal ulceration, and epithelial and anterior stromal thinning.

FIG. 1 shows a histogram which sets out the percentage of animals in each implanted group with corneal ulcers. Forty three percent of animals implanted with a membrane having a porosity of 25 nm showed corneal ulceration. Eighty percent of animals implanted with a membrane have a pore size of 15 nm exhibited corneal ulceration. Effectively the same result was observed for the cuprophan and gambrane membranes which have a pore size of approximately less than 1.5 nm. No ulceration was seen in animals implanted with membranes having pore sizes of 50 nm and 100 nm.

FIG. 2 shows a histogram which sets out the percentage of animals with epithelial and anterior stromal thinning following ocular implantations of membranes of varying pore size. FIG. 2 clearly shows that as the pore size of the implanted membrane decreases, the number of animals with epithelial and anterior stromal thinning increases. All animals implanted with membranes having a pore size of 15 nm or less exhibited epithelial and anterior stromal thinning. Membranes having a pore size of 25 nm resulted in 75% of animals showing epithelial and anterior stromal thinning. This figure fell to 31% and 27% respectively for membranes having a pore size of 50 nm and 100 nm.

FIGS. 1 and 2 clearly show that the pore size of corneal onlays for the insertion into the eyes of animal should be greater than about 15 nm.

EXAMPLE 3

Corneal Epithelial Tissue Requires Trophic Factors of a Molecular Weight Greater Than 10,000 Daltons for Cell Attachment, Migration and Epithelial Outgrowth In this experiment the requirement for access to tissue fluid factors, as exemplified by serum, to enable the optimal proliferative and migratory responses of corneal epithelial cells was determined. Corneal epithelial cells were maintained in a culture medium (serum-free) which provided for the requirements of the cells for glucose, nutrients, metabolites and small physiological molecules. The purpose of the experiment was to determine the requirement of these cells for tissue trophic factors, in order to permit certain cellular functions that would enable the colonisation of a corneal implant with corneal epithelium and for the maintenance of that epithelial tissue. This was demonstrated by examining the effect of the addition to the culture medium of serum, as an example of such tissue fluids, upon migratory and outgrowth activities of corneal epithelial cells.

As the purpose of the experiments was to determine the requirement of corneal epithelial cells for factors with a trophic effect, the experiments were designed in a manner to remove the possibility that any stimulatory effect of serum factors could arise solely due to direct stimulation of cell attachment following adsorption of the serum factors onto the polymer surface. Two tissue and serum factors, fibronectin or vitronectin, can be found in a soluble form and can also adsorb onto surfaces, and in this insoluble form can serve to promote cellular attachment. In order to distinguish between nutrient or trophic support from serum factors, as distinct from stimulation of cellular adhesion to the culture surface as a result of adsorption onto that surface of serum fibronectin and/or vitronectin, the serum used in these experiments was exhaustively depleted of the adhesive proteins fibronectin and vitronectin prior to use in the cell assays.

The cell culture assay system used for the determination of the effect of tissue trophic factors was chosen to represent the corneal onlay material of the prior art, in being supportive of the processes of initial cell attachment. The corneal epithelial cells were cultured on the synthetic polymer surface called tissue culture polystyrene, which is an oxidized polystyrene surface that has been optimized for support of cellular attachment. In having a surface chemistry that is supportive of the attachment of corneal epithelial cells, this polymer surface resembles that of an example of a corneal onlay described in the prior art, insofar as cell adhesion is concerned.

It has previously been proposed that extracellular matrix components such as fibronectin, laminin or collagens may stimulate the cellular attachment activity of corneal epithelial cells. In preliminary experiments, different extracellular matrix components were compared for their ability to support the initial attachment and outgrowth of corneal epithelial cells when the factors were adsorbed onto a culture surface, in order to determine an optimal surface for the stimulation of corneal epithelial cell migratory activity. In these preliminary experiments, the culture medium used was serum-free medium containing 20% (v/v) foetal calf serum depleted of both Fibronectin and Vitronectin, in order that the effectiveness of the different extracellular matrix components may be determined without any contribution from vitronectin or fibronectin adsorbed from the serum component of the culture medium.

In order to investigate the migratory response of bovine corneal epithelial cells to the various extracellular matrix components, it was appropriate to determine the rate of outgrowth of cells from a cell island. This was achieved by seeding cells onto a defined central region of the culture surface (tissue culture polystyrene) of a known diameter at a predetermined cell concentration, sufficient to produce a confluent monolayer of epithelial cells at the commencement of the culture period. The restricted area was established by using stainless steel (s/s) rings that have a v-profile silicone O-ring at the base, which effectively provided a sealed chamber into which the cells can be loaded. After seeding and culture for sufficient time for the cells to attach (four hours culture), the rings were removed and fresh culture medium applied. The cells in the epithelial island were then free to grow out over the surface, at a rate that could be determined in part by the extracellular matrix component that had been preadsorbed onto the polymer surface. In this assay, two different formats were possible. Cells may be seeded either within the region of the central chamber thereby effectively creating a circular island of cells, or alternatively outside the chamber and so leaving a central region of the surface devoid of cells. Using these assay formats, the extracellular matrix components were compared for their influence upon the outgrowth of epithelial cells.

EXPERIMENTAL

Preparation of Surfaces of Extracellular Matrix Components

Five different defined matrices have been tested for their ability to support attachment of corneal epithelial cells, by pre-adsorbing the following proteins onto tissue culture polystyrene and then blocking any residual protein binding sites with 1% (w/v) solution of bovine serum albumin:

1. Bovine serum vitronectin at 5 µg/ml (Isolated as previously described);
2. Bovine serum fibronectin at 10 µg/ml. (from Sigma);
3. Murine laminin at 50 µg/ml. (Purified from EHS sarcoma, provided from Collaborative Biomedical);
4. Murine Collagen Type IV at 1.5 µg/ml. (Purified from EHS sarcoma, provided from Collaborative Biomedical);
5. Bovine Collagen Type I at 1.5 mg/ml. (Purified from bovine calf skin, "Cellagen" from ICN).

These precoating concentrations were chosen to be levels that would offer maximal stimulation of cell adhesion. 80 µl of matrix solution were added at the predetermined concentrations to replicate tissue culture polystyrene wells (96-well culture trays) and incubated for one hour at 37° C. The matrix solutions were then removed and the surfaces 'blocked' with a solution of 1% (w/v) bovine serum albumin in serum-free culture medium and incubated for one hour at 37° C. This 'blocking' step ensures that all non-matrix supplied cell binding sites are effectively neutralized prior to cell seeding. The blocked tissue culture polystyrene surface was also included in each assay and, as a result of the treatment with albumin, served as an effective negative control.

Cell Attachment Assay:

One hundred µl aliquots of $0.7$–$1.0 \times 10^5$ cells/ml for cultured cells, or $3.0$–$5.0 \times 10^5$ cells/ml for primary cells in 1% (w/v) bovine serum albumin in serum-free culture medium, were added to each well and incubated for ninety minutes at 37° C. Cell adhesion was determined by methylene blue staining and absorbances read at 650 nm on a plate-reader. Collagen Type I was used as the reference substrate for each cell origin type and cell attachment set at 100%, and so for the purposes of reporting, cell adhesion to all other matrices was expressed as a percentage of that on the Collagen Type I in the same experiment.

Cell Outgrowth Assay:

One hundred µl aliquots of cultured bovine corneal epithelial cells (passage numbers 5 to 7) of limbal origin were seeded at $5 \times 10^5$ cells/ml into the centre of the stainless steel migration fences, or 0.45 ml aliquots of cell suspension at $1 \times 10^6$ cells/ml seeded around the outside of the fences. These concentrations were sufficient to give a uniform monolayer of attached cells after four hours incubation. Cells were incubated for four hours at 37° C. before removal of the fences. The culture medium used was 20% (v/v) feotal bovine serum, depleted of fibronectin and vitronectin, in 40% (v/v) Dulbecco's Minimal Essential Medium, 40% (v/v) Ham's F12 medium.

Each treatment was conducted in triplicate using the following surface coatings:

a) Fibronectin—fibronectin, precoated at 10 µg/ml;

b) Ln—laminin, precoated at 25 µg/ml c) CI—collagen type I, precoated at 187.5 µg/ml The precoatings were incubated for one hour at 37° C. prior to use. During the culture period, the culture medium was changed every third day.

The outgrowth index was calculated as:

$$\text{Outgrowth Index} = \frac{\text{five (or seven) day cell outgrowth area} \times 10}{\text{initial four hour cell area}}$$

RESULTS

1. Response of Cultured Cells—Initial Cell Attachment

For cells that had been in culture for a short period (passage numbers 2–3), each of the extracellular matrix molecules fibronectin, vitronectin, collagen I, collagen IV, and laminin, were stimulatory of initial cell attachment. The results with cells that were freshly prepared from tissue, primary cell suspensions, were similar but the responsiveness of these cells to vitronectin was relatively poor. In three experiments purified extracellular matrix components were compared for the attachment, during the fast ninety minutes of culture, of bovine corneal epithelial cells which were used immediately after isolation from the cornea. Collagen I, laminin and collagen IV each stimulated attachment of corneal epithelial cells. Taken over a series of eight experiments, fibronectin was also stimulatory of attachment of cells from each region, but for each cell origin the response of these primary isolates towards fibronectin was variable from experiment to experiment (mean response varying over a 2.3 to 2.8 fold range). Vitronectin, although stimulatory, was consistently much less effective than laminin, the collagens or fibronectin in promoting cell attachment of each of these primary isolate cells. This is a surprising finding insofar as vitronectin is concerned.

2. Effects of Extracellular Matrix Components on the Migration of Cultured Corneal Cells i) Cell outgrowth from a centrally seeded area.

Table 7 shows the comparison of different extracellular matrix treatments for cell outgrowth from the epithelial cell islands over a five to seven day culture period. In view of the poor performance of vitronectin for the stimulation of attachment of primary corneal epithelial cells to vitronectin, this factor was not included in the comparison. Some interesting differences between the different extracellular matrix treatments are apparent. In the presence of serum depleted of both fibronectin and vitronectin, surfaces coated with either fibronectin or Collagen type I performed well in terms of area covered by cells moving out from a central island. The laminin coated surfaces, however, performed poorly relative to the other surfaces.

TABLE 7

Effects of Extracellular Matrix Components on the Migration of Cultured Corneal Cells - Cell Outgrowth from a Centrally Seeded Island

| | Surface medium | Index (Mean ± SD) |
|---|---|---|
| Culture period five days: | TCPS/NS | 3.4 ± 0.0 |
| | Fn/DD | 3.2 ± 0.0 |
| | Ln/DD | 1.6 ± 0.8 |
| | Col I/DD | 2.2 ± 0.3 |
| Culture period seven days: | TCPS/NS | 5.4 ± 0.5 |
| | Fn/DD | 4.7 ± 0.3 |
| | Ln/DD | 2.3 ± 0.3 |
| | Col I/DD | 4.2 ± 0.4 |

In Table 7 the following abbreviations are used:
TCPS = tissue culture polystyrene
NS = foetal calf serum (not depleted of fibronectin or vitronectin)
Fn = fibronectin
Ln = laminin
Col I = collagen I
DD = foetal calf serum, depleted of both fibronectin and vironectin ii) Cell Ingrowth from a Peripherally Seeded Ring.

Corneal epithelial cells seeded around the outside of the fences were monitored, until one replicate of any treatment had completely covered the central area of the well. The effectiveness of each treatment was calculated and expressed as a percentage of the central area that was covered at the end of the experimental period. Table 8 shows the comparison of different extracellular matrix treatments for cell outgrowth from the epithelial cell islands over a seven day culture period. This format gave similar results to those found on the central seeding method. Laminin again proved to be a poor surface for the promotion of migratory activity, but Fibronectin and collagen I were effective in stimulating cell migration.

TABLE 8

Effects of Extracellular Matrix Components on the Migration of Cultured Corneal Cells - Cell Ingrowth from a Seeded Ring of Cells

| Surface/Medium | 5% Ingrowth * (Mean ± SD) |
|---|---|
| TCPS/NS | 94.4 ± 5.7 |
| Fn/DD | 95.6 ± 5.7 |
| Ln/DD | 52.9 ± 7.9 |
| Col I/DD | 95.4 ± 4.8 |

In Table 8 the following abbreviations are used:
TCPS = tissue culture polystyrene
NS = foetal calf serum (not depleted of fibronectin or vitronectin)
Fn = fibronectin
Ln = laminin
Col I = collagen I
DD = foetal calf serum, depleted of both fibronectin and vitronectin
Mean of four hours initial uncovered
* $\frac{\text{area-seven day uncovered area} \times 10}{\text{Mean four hour initial uncovered areas}}$ These preliminary experiments showed that both fibronectin and collagen I are stimulatory of both the initial cell attachment of corneal epithelial cells to polymer surfaces and also the outgrowth and migration of the cells from cell islands. For the experiments in which the effect of serum trophic factors was to be determined, the fibronectin-coated polymer surface was included as being representative of a surface containing a biological adhesive factor.

Determination of the molecular weight of serum trophic factor(s) that support the migration and outgrowth of corneal epithelial cells

EXPERIMENTAL

Fractionation of serum

Foetal bovine serum was depleted of the cell-adhesive molecules vitronectin (Vitronectin) and fibronectin (Fibronectin) by the methods we have previously described. This depleted Fibronectin and Vitronectin-depleted serum was then passed through a series of ultra-filtration membranes, in order to separate the serum components into fractions containing components of defined ranges of molecular weights. Three different non-ionic Amicon ultra-filtration membranes were used:

1. Amicon PM10 membrane, with a molecular weight cut-off at 10,000 daltons;
2. Amicon PM30 with a molecular weight cut-off of 30,000 daltons;
3. Amicon XM100 with a molecular weight cut-off at 100,000 daltons.

The membranes were cleaned prior to use as per the manufacturer's recommendations. The membranes were each pretreated with a solution of 1% (w/v) bovine serum albumin in PBS, followed by a wash with sterile PBS, in order to reduce nonspecific binding of proteins onto the membrane surface and consequental loss of serum components, during the subsequent filtration step. The various membranes were held in an ultrafiltration assembly (Amicon) and the Fibronectin and Vitronectin-depleted serum or fraction thereof was stirred with a magnetic stirrer and filtered at an air pressure of 400 kPa.

The fractionation of the serum was performed by the following method:

The Fibronectin and Vitronectin-depleted serum was diluted with two volumes of sterile phosphate-buffered saline (PBS) and put through a series of sequential filtrations. All of the Fibronectin and Vitronectin-depleted and diluted serum was firstly passed through a 43 mm diameter XM100 membrane and the filtrate collected. The retentate from this membrane was discarded. Two aliquots of the filtrate from the XM100 membrane were taken and passed through either a PM10 or a PM30 25 mm diameter membrane. The filtrates from these two membranes separately collected and the retentates of these membranes were discarded. Low molecular weight components were removed from these filtrate fractions and the remainder of the components in the fractions were concentrated back down to a volume that was calculated to be equal to the volume if they had not been diluted (and assuming full recovery), by treatment upon a 43 mm diameter Amicon UM2 membrane with an exclusion cutoff of 1,000 daltons. There were, therefore, the following fractions.

Fraction 1: The filtrate of the XM100 membrane that was subsequently retained upon the UM2 membrane—this preparation would contain components in the 1,000–100,000 daltons range.

Fraction 2: The filtrate from the XM100 membrane that was also a filtrate of the PM30 membrane but was subsequently retained upon the UM2 membrane—this preparation would contain components in the 1,000–30,000 daltons range.

Fraction 3: The filtrate from the XM100 membrane that was also a filtrate of the PM10 membrane but was subsequently retained upon the UM2 membrane—this preparation would contain components in the 1,000–10,000 daltons range.

Each of these fractions were sterilized after preparation by passage through a Gelman 'Acrodisc'™ 0.22 μm filter. The serum fractions were run on a 12.5% polyacrylamide mini-gel (BioRad Protean II) under non-reducing conditions, to confirm the efficacy of the filtration procedures, and the protein concentration for each fraction was determined according to standard procedures.

Assay of Effects of Serum and Serum Fractions upon Corneal Epithelial Cell Growth and Migration The Fibronectin and Vitronectin-depleted serum and depleted serum fractions, prepared as described above, were added to the culture medium (1:1 Dulbecco's Modified Essential Medium/Ham's F12 serum-free culture medium) at a concentration of 20% (v/v) in order to study the effects of the various fractions upon the attachment and growth of bovine corneal epithelial cells and the assays were conducted over a culture period of six days.

Culture wells were set up with sterile stainless steel "fences" which were contained within the wells and centrally located. Aliquots (100 μl) of a cell suspension of corneal epithelial cells (prepared from bovine corneal tissue) were each seeded into stainless steel "fence" enclosure at a density of $5 \times 10^5$ cells/ml. This cell loading was sufficient to give a confluent monolayer twenty four hours after seeding the cells into the culture area defined by the lumen of the fence, in a culture medium that contained intact serum. In these experiments the fences were removed from the culture wells after twenty four hours culture, then the culture medium volume adjusted and the culture allowed to continue.

Each test sample of Fibronectin and Vitronectin-depleted serum fraction was assayed in triplicate wells, with one well being for quantitation of the area of the culture containing cells after a twenty four hour culture period, and two wells being used for measuring the area after seven days culture. At the appropriate time-point, the cells were fixed with formol-saline and stored in sterile PBS at 4° C. until required. The cell density was determined by staining with Methylene Blue after Oliver et al., and the amount of bound stain measured colourimetrically at 655 nm on a plate-reader. Methylene blue staining was used to determine both cell outgrowth areas (by image analysis using a Quantimet 570 image analyser, detecting cells by the increased colour following uptake of the blue stain), and to measure the extent of cell proliferation (determined colourimetrically at 655 nm, on an immunoassay plate reader).

The culture media combinations were:

i) serum-free culture medium, to which was added 20% (v/v) of Fraction 3, having serum factors of 1000 to 10,000 daltons in size;

ii) serum-free culture medium, to which was added 20% (v/v) of Fraction 2 having serum factors of 1000 to 30,000 daltons in size;

iii) serum-free culture medium, to which was added 20% (v/v) of Fraction 1, having serum factors of 1000 to 100,000 daltons in size;

iv) serum-free culture medium, to which was added 20% (v/v) of a combination of Fractions 1, 2 and 3, having serum factors of 1000 to 100,000 daltons in size;

v) serum-free culture medium+20% (v/v) Fibronectin- and Vitronectin-depleted serum (not fractionated as to size).

vi) serum-free medium alone.

As described above, two culture surfaces were used: firstly, tissue culture polystyrene, and secondly, tissue culture polystyrene that had been precoated with bovine serum Fibronectin at 10 μg/ml and incubated for one hour at 37° C. prior to cell loading.

RESULTS

By separating Fibronectin and Vitronectin-depleted serum into fractions containing known molecular weight ranges, it was possible to assess the effects of serum components, within specific molecular weight ranges, upon corneal epithelial cell attachment, migration and outgrowth.

FIG. 3 shows the effect of the different fractions prepared from Fibronectin and Vitronectin-depleted serum upon the attachment of c0meal epithelial cells during the first twenty four hour of culture. In the manner in which this experiment was conducted, the number of cells present on the surfaces in the different treatments were close to being the same for each treatment after twenty four hour of culture. The different treatments could therefore be compared for the rates of cell outgrowth and increase in cell number beyond the initial twenty four hour culture period, having a similar population of cells in the assay at the twenty four hour time point.

FIG. 4 shows the effects of these various fractions upon the area of the culture surface covered with cells during a six day culture period, expressed as the cell outgrowth index (calculated as described above). FIG. 4 also compares these results in a manner that relates the increase in cell culture area over the six day culture period (expressed as a ratio of that at twenty four hours) to the cell attachment data (at twenty four hours).

Cell migration and outgrowth of the island was evident on all the medium/surface combinations, but to markedly different extents. On average, in the treatments containing Fibronectin- and Vitronectin-depleted foetal calf serum (the positive control) or the treatment containing 20% (v/v) of serum Fraction 1 having serum factors of 1000 to 100,000 daltons in size, the cells migrated out to cover an area approximately ten times larger than those covered by the cells in the treatments containing Fractions 2 or 3. Furthermore, corneal epithelial cells cultured in the treatment containing recombined Fractions 1, 2 and 3 migrated out to cover about 33% of the area of the positive control combination on both tissue culture polystyrene and fibronectin coated tissue Culture polystyrene.

FIG. 4 makes an interesting comparison between the different serum fractions. Similar levels of cell attachment after twenty four hours culture were seen with the treatments having either serum-free medium alone, or serum-free medium containing 20% (v/v) Fraction 3 (having serum factors of 1000 to 10,000 daltons in size) or 20% (v/v) of Fraction 2 (having serum factors of 1000 to 30,000 daltons in size) or 20% (v/v) of Fraction 1 (having serum factors of 1000 to 100,000 daltons in size) or the recombination of Fractions 1, 2 and 3. Notwithstanding the initial cell attachment being equivalent for these different treatments, there was a marked difference in the increase in cell area. Only the treatment containing 20% (v/v) of Fraction 1 (serum factors of 1000 to 100,000 daltons in size) and the treatment containing the recombination of Fractions 1, 2 and 3, provided for increased cell area over the six day culture on tissue culture polystyrene. The same result was seen for these treatments with the surface of Fibronectin-coated tissue culture polystyrene.

In using these two examples of culture substrata as well as in using a culture medium that provides for the small molecular weight requirements of the cells, the experimental format used in these experiments is representative of corneal onlays previously described, providing for both cellular access to nutrients and other small molecules and also providing for a surface chemistry that supports corneal epithelial cell attachment. Taken together, these results indicate that there is/are tissue trophic factors, as exemplified by factor(s) in serum, that are required for optimal epithelial cell coverage of a synthetic polymer surface such as the tissue culture polystyrene surface. These factor (s) are greater than 1000 daltons in size and are also retained on filters that exclude molecules of 10,000 and greater. These results indicate that the activity, or a portion thereof, can be identified as falling within the molecular weight range of 10,000 to 75,000 daltons (determined from being excluded by the Amicon PM10 membrane filter and included by the Amicon XM100 membrane filter). These serum factors are not the adhesion factors Fibronectin or Vitronectin.

These results indicate that there is a requirement of corneal epithelial cells for trophic factors from tissue, for the activities of cell outgrowth and migration onto a surface. Tissue factors such as serum stimulate epithelial cell outgrowth from epithelial islands, and this effect is not dependent upon the serum adhesive proteins fibronectin and vitronectin. By molecular weight fractionation of the serum, this activity has been shown to be greater than 10,000 daltons in size. Hence, the corneal onlays according to this invention have a porosity sufficient to allow passage therethrough of tissue fluid components having a molecular weight greater than 10,000 daltons.

EXAMPLE 4

Corneal Onlay Preparation

Corneal onlays may be prepared from a polymer comprising crosslinked macrocycles that are made up of units of the following formula

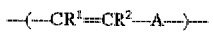

wherein A is alkylene or alkenylene each having from 3 to 10 carbon atoms and each of which may be substituted by one or more $R^3$ radicals, each of $R^1$ and $R^2$, independently of the other, is hydrogen or lower alkyl, and $R^3$ is lower alkyl, fluorinated lower alkyl or a siloxane radical. Such polymers are described in EP-A-501,917 which is incorporated herein by reference in its entirety.

In a first experiment, 5% tert-butylper-2-ethylhexanoate is added to poly(1-octene-1,8-diyl) (trade name Vestenamer®) and the crossing agent is incorporated in a customary commercial kneader under reduced pressure at a temperature of 35° C. Cornal onlays are compression molded from the resulting mass at 160° C. and a pressure of 5 to 20 bars for a period of five minutes using suitable dyes. The corneal onlays so obtained have an oxygen permeability (Dk) of 106 and a tear strength of 2.7 MPa. Pores are formed in the onlays using a microprocessor controlled pulse laser. In the optical axis region of each onlay a plurality of pores having a diameter of about 200 nm are formed. Outside of the optical axis region of each onlay a plurality of pores having a diameter of about 200 microns are formed.

In a second experiment onlays are prepared from copolymers of the formula I as described in EP-A-538,188, which is incorporated herein by reference in its entirety. Specifically, 100 mmol of tricyclo[$1.1.1.0^{1,3}$]pentane and 150 mmol of ethyl acrylate are copolymerized for two days in diethyl ether at room temperature, excluding oxygen. A sheet with a glass transition temperature of 100° C. is obtained. The sheet is compression molded to give corneal onlays. Pores are formed in the onlay as described as above.

Patent and other technical sources referred to herein are incorporated by reference into this specification.

The invention herein described is subject to variation, as will be appreciated by the skilled addressee, without departing from its spirit or scope. All such variations are embraced by this invention.

I claim:

1. A corneal onlay for use in surgical implantation into or onto the cornea of a mammal, said onlay having an optical axis region with optical characteristics which provide visual acuity therethrough, said onlay being comprised of a non-biodegradable non-hydrogel ocularly biocompatible material, and characterized in that said onlay has a porosity sufficient to allow passage therethrough of tissue fluid components having a molecular weight greater than 10,000 daltons, thereby providing for a flux of tissue fluid between cells anterior of the implanted onlay and cells posterior thereof, wherein the porosity of the optical axis region is such that it allows the flux of tissue fluid components whilst excluding ingrowth of ocular tissue, and wherein said onlay is adapted for epithelial recolonization.

2. A corneal onlay according to claim 1 wherein the periphery of the onlay surrounding the optical axis region defines a skirt having a porosity sufficient to permit ingrowth of ocular tissue so as to facilitate anchoring of the onlay to the cornea.

3. A corneal onlay according to claims 1 or 2 wherein the surface of the onlay is modified so as to stimulate the adhesion of cells adjacent to the implanted onlay.

4. A corneal onlay according to claim 2 wherein the onlay is coated with one or more components which promote the growth of tissue adjacent to the implanted onlay, and/or cell adhesion to the onlay.

5. A corneal onlay according to claim 1 wherein porosity of the onlay is provided by a plurality of pores having a size sufficient to allow passage through the onlay of proteinaceous tissue fluid components having a molecular weight greater than 10,000 daltons but which excludes tissue ingrowth.

6. A corneal onlay according to claim 2 wherein porosity of the visual optical axis is provided by a plurality of pores having a size sufficient to allow passage through the onlay of proteinaceous tissue fluid components having a molecular weight greater than 10,000 daltons but which excludes tissue ingrowth.

7. A corneal onlay according to claims 5 or 6 wherein said plurality of pores comprise a diameter from 15 nanometers to 0.5 micrometers.

8. A corneal onlay according to claim 7 wherein said plurality of pores comprise a diameter from 15 nanometers to 300 nanometers.

9. A corneal onlay according to claim 8 wherein said plurality of pores comprise a diameter from 20 to 150 nanometers.

10. A corneal onlay according to claim 2 wherein said porosity of the skirt is defined by a plurality of pores having a diameter of at least 20 microns so as to allow tissue ingrowth and anchorage of the onlay.

11. A corneal onlay according to claim 10 wherein the skirt is formed of a different biocompatible non-biodegradable material than the optical axis region, and wherein said skirt is either integral with the optical axis region or secured to the periphery thereof.

12. A method for correcting the optical properties of an eye or altering the appearance thereof comprising surgically implanting into or onto the cornea a corneal onlay having optical characteristics which provide visual acuity therethrough, said onlay being comprised of a corneal onlay for use in surgical implantation into or onto the cornea of a mammal, said onlay having an optical axis region with optical characteristics which provide visual acuity therethrough, said onlay being comprised of a non-biodegradable non-hydrogel ocularly biocompatible material, and characterized in that said onlay has a porosity sufficient to allow passage therethrough of tissue fluid components having a molecular weight greater than 10,000 daltons, thereby providing for a flux of tissue fluid between cells anterior of the implanted onlay and cells posterior thereof, wherein the porosity of the optical axis region is such that it allows the flux of tissue fluid components whilst excluding ingrowth of ocular tissue, and wherein said onlay is adapted for epithelial recolonization.

13. A method according to claim 12 wherein the periphery of the onlay surrounding the optical axis region defines a skirt having a porosity sufficient to permit ingrowth of ocular tissue so as to facilitate anchoring of the onlay to the cornea.

14. A method according to claim 12 wherein the surface of the onlay is modified so as to stimulate the adhesion of cells adjacent to the implanted onlay.

15. A method according claim 12 wherein the onlay is coated with one or more components which promote the growth of tissue adjacent to the implanted onlay, and/or cell adhesion to the onlay.

16. A method according to claim 12 wherein porosity of the onlay is provided by a plurality of pores having a size sufficient to allow passage through the onlay of proteinaceous tissue fluid components having a molecular weight greater than 10,000 daltons but which excludes tissue ingrowth.

17. A method according to claim 13 wherein porosity of the visual optical axis is provided by a plurality of pores having a size sufficient to allow passage through the onlay of proteinaceous tissue fluid components having a molecular weight greater than 10,000 daltons but which excludes tissue ingrowth.

18. A method according to claims 16 or 17 wherein said plurality of pores comprise a diameter between 15 nanometers to 0.5 micrometers.

19. A method according to claim 18 wherein said plurality of pores comprise a diameter between 15 nanometers to 300 nanometers.

20. A method according to claim 18 wherein said plurality of pores comprise a diameter between 20 to 150 nanometers.

21. A method according to claim 13 wherein said porosity of the skirt is defined by a plurality of pores having a diameter of at least 20 microns so as to allow tissue ingrowth and anchorage of the onlay.

22. A method according to claim 13 wherein the skirt is formed of a different biocompatible non-biodegradable material than the optical axis region, and wherein said skirt is either integral with the optical axis region or secured to the periphery thereof.

23. A method according to claim 12 wherein said onlay is transplanted into the epithelium of the cornea.

24. A method according to claim 23 wherein the onlay is positioned adjacent the basement membrane of the cornea.

25. A method according to claim 13 wherein the optical axis region is coloured.

26. A corneal onlay as claimed in claim 1 for use in a method as claimed in claim 12.

* * * * *